US007351375B2

United States Patent
Noda et al.

(10) Patent No.: US 7,351,375 B2
(45) Date of Patent: Apr. 1, 2008

(54) IMPLEMENT AND DEVICE FOR ANALYSIS (75) Inventors: Norimasa Noda, Kyoto (JP); Koji Katsuki, Kyoto (JP); Kotaro Kado, Kyoto (JP)

(73) Assignee: Arkray, Inc., Kyoto (JP)

( * ) Notice: Subject to any disclaimer, the term of this patent is extended or adjusted under 35 U.S.C. 154(b) by 824 days.

(21) Appl. No.: 10/483,442

(22) PCT Filed: Jul. 16, 2002

(86) PCT No.: PCT/JP02/07239

§ 371 (c)(1),
(2), (4) Date: Jan. 9, 2004

(87) PCT Pub. No.: WO03/008956

PCT Pub. Date: Jan. 30, 2003

(65) Prior Publication Data
US 2004/0173458 A1   Sep. 9, 2004

(30) Foreign Application Priority Data
Jul. 18, 2001 (JP) .............................. 2001-218021

(51) Int. Cl.
*G01N 33/00* (2006.01)
(52) U.S. Cl. ........................ 422/82.01; 422/50; 422/55; 422/58; 422/99
(58) Field of Classification Search .................. 422/50, 422/55, 58, 68.1, 82.01, 99
See application file for complete search history.

(56) References Cited

U.S. PATENT DOCUMENTS 5,264,103 A    11/1993  Yoshioka et al.
5,580,435 A *  12/1996  Kovacs .................... 204/603
2002/0189941 A1  12/2002  Katsuki et al.

FOREIGN PATENT DOCUMENTS

| EP | 0 417 796 | 9/1990 |
| EP | 0 690 134 | 1/1996 |
| EP | 1 203 959 | 8/2000 |
| EP | 1 114 996 | 7/2001 |
| JP | 8-193969 | 7/1996 |
| JP | 10-170471 | 6/1998 |
| JP | 10-311814 | 11/1998 |
| JP | 11-118794 | 4/1999 |
| JP | 11-352093 | 12/1999 |
| JP | 2000-258382 | 9/2000 |
| JP | 3260739 | 12/2001 |
| JP | 2002-055069 | 2/2002 |
| WO | WO 99/32881 | 7/1999 |
| WO | WO 00/60340 | 10/2000 |
| WO | WO 01/36954 | 5/2001 |

* cited by examiner

*Primary Examiner*—Jill Warden
*Assistant Examiner*—Samuel P Siefke
(74) *Attorney, Agent, or Firm*—Hamre, Schumann, Mueller & Larson, P.C.

(57) ABSTRACT

The present invention relates to an analyzing implement (1) having a capillary for movement of a specimen liquid. The capillary has inner surfaces (21*c*, 32*c*) provided with a first and a second opposed electrodes opposed to each other. The implement (1) includes, for example, a substrate (20), a cover (40) and a spacer (30) between the substrate (20) and the cover (40). In this case, the capillary is provided by the substrate (20), the cover (40) and the spacer (30). Preferably, capillary forming surfaces (31*c*, 32*c*) of the spacer (30) are electrically conductive, in which case the surfaces (31*c*, 32*c*) provide the first and the second electrodes.

10 Claims, 9 Drawing Sheets

IMPLEMENT AND DEVICE FOR ANALYSIS

TECHNICAL FIELD

The present invention relates to a technology for measurement of at least one of the followings: a concentration level of a specific component in a specimen liquid (e.g. a glucose concentration in a body fluid such as blood), and a physical quantity correlating to an amount of coexisting component in the specimen liquid.

BACKGROUND ART

For a purpose of measuring blood sugar levels privately at home and elsewhere, palm-size, portable blood sugar level testers are used widely. When measuring the blood sugar level with these handy-type blood sugar level testers, a biosensor which serves as an enzyme reaction field must be attached to the level tester, and then the blood must be supplied to the biosensor.

Blood contains solid component (blood cells), and it is known that the amount of blood cells influences the measurement. In order to overcome this, some methods of measurement include steps of measuring the percentage of blood-cell component (hematocrit value) in the blood, and correcting the calculated blood sugar level in accordance with the hematocrit value.

The hematocrit value can be measured, for example, by using methods disclosed in the Japanese Patent Laid-Open No. 11-118794 and the Japanese Patent Laid-Open No. 2002-55069. In each method, the hematocrit value is measured by correlation to the level of electric conductivity (resistance).

Figure 10A:
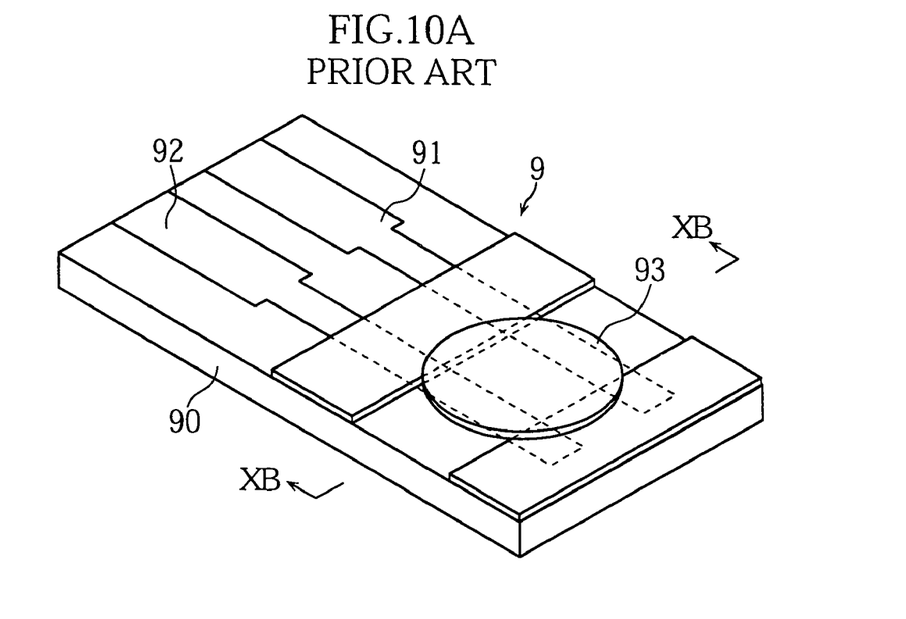
FIG. 10A is an overall perspective view showing a conventional hematocrit measuring element.
Figure 10B:
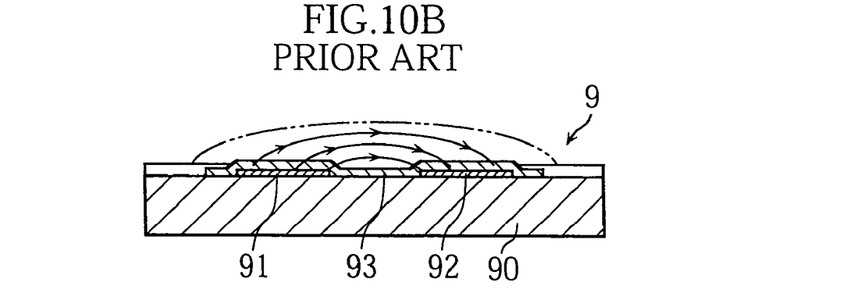
FIG. 10B is a sectional view taken in lines XB-XB in FIG. 10A.

The method disclosed in the Japanese Patent Laid-Open No. 11-118794 uses a hematocrit value measuring element to measure the hematocrit value of blood. As shown in FIG. 10A and FIG. 10B, a hematocrit value measuring element 9 includes a substrate 90 formed with a pair of electrodes 91, 92 spaced from each other on the same plane, and a layer of reagent 93 covering a pair of ends of the electrodes 91, 92.

Figure 11:
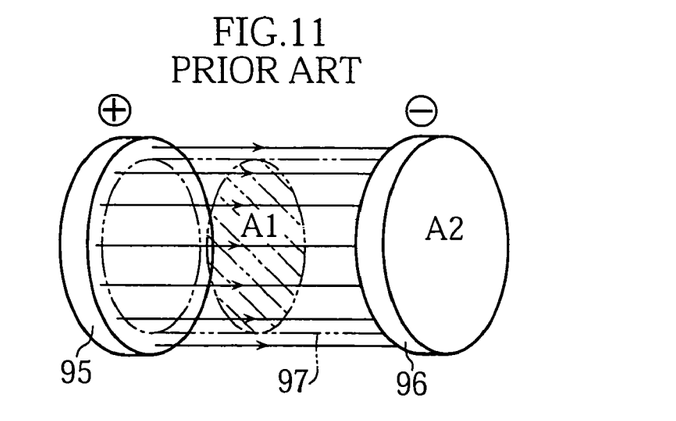
FIG. 11 is a perspective view for describing an electric conductivity measuring system ideal for the liquid phase.

In a liquid phase such as blood, ions in the liquid serve as a carrier in electric charge transfer, and therefore in order to measure the level of electric conductivity of a liquid phase at a high accuracy, appropriate movement of the carrier is necessary between the electrodes. For this purpose, as shown in, a conceptual drawing in FIG. 11, electric lines of force between electrodes 95, 96 should desirably be uniform. In order to provide uniform electric lines of force, it is necessary that the measuring electrodes 95, 96 are opposed to each other, and that an area of the opposed surface (A2) in the electrodes 95, 96 must be greater than or equal to an area of the section (A1) of a body of an object liquid 97.

However, as clearly shown in FIG. 10A and FIG. 10B, the electrodes 91, 92 in the hematocrit measuring element 9 are spaced in the same plane, and therefore are not opposed to each other. This leads to an electric conductivity measurement based on a localized-carrier movement due to non-uniform electric lines of force. As a result, it is impossible to accurately measure the electric conductivity, nor the hematocrit value derived therefrom.

In the above method, the hematocrit value measurement is made using the hematocrit value measuring element 9, which is a separate implement from the biosensor implement which is for the measurement of blood sugar level. This poses another problem of increased cost in measurement incurred by the needs for two analyzing implements for a single measurement of the blood sugar level. Still another problem is inconvenience, i.e. the hematocrit value measurement using the hematocrit value measuring element 9 and the blood sugar level measurement using the biosensor must be made separately by replacing the hematocrit value measuring element 9 with the biosensor.

On the other hand, in the method disclosed in the Japanese Patent Laid-Open No. 2002-55069, a blood tester uses a blood sampling probe having a double-wall construction provided by an inner tube and an outer tube, and each of the inner tube and the outer tube has a tip serving as an electrode for measurement of the electric conductivity of blood.

This method is primarily for a large apparatus such as one having a sampling probe, and is not a technique applicable to a combination of a handy-type blood sugar level tester and a biosensor.

DISCLOSURE OF THE INVENTION

It is an object of the present invention to provide a simple method of reducing the influence of the hematocrit value, for accurate measurement of the concentration level.

A first aspect of the present invention provides an analyzing implement including a capillary for movement of a specimen liquid. The capillary has an inner surface provided with a first and a second opposed electrodes opposed to each other.

The implement according to the present aspect includes, for example, a substrate, a cover covering the substrate, and a spacer between the substrate and the cover. In this case, the capillary is formed by the substrate, the cover and the spacer. Surfaces of the spacer forming the capillary are electrically conductive and provide the first and the second opposed electrodes.

The spacer includes, for example, two blocks opposed to each other. In this case each block is preferably formed entirely of an electrically conductive material. Each block is formed of an electrically insulating resin containing an electrically conductive polymer or an electrically conductive filler, or of a metal.

Alternatively however, each block may include an electrically insulating part and an electrically conductive part, and the electrically conductive parts of the pair of spacers serve as the first and the second electrodes. The spacer may be a single member having a slit. In this case, the first and the second electrodes are provided in mutually opposing surfaces in the slit.

Each block has, for example, a rectangular cross section defined by an upper surface, a lower surface and two side surfaces, with the upper surfaces and the lower surfaces being adhesive. In this case, the cover is bonded to the substrate via the two blocks. In other words, the spacer may serve as an adhesive layer for the cover to be bonded to the substrate.

The first and the second opposed electrodes are for measurement of e.g. a dielectric constant, a resistance value or a physical quantity correlating to electrical conductivity of the specimen liquid.

The analyzing implement according to the present aspect preferably further includes a first and a second electrodes for measurement of a physical quantity correlating to concentration of a specific component of the specimen liquid.

The analyzing implement according to the present aspect includes, for example, a first through a fourth leads formed on the substrate. In this case, the capillary is formed by the substrate, the cover and the spacer. Surfaces of the spacer forming the capillary are electrically conductive and provide the first and the second opposed electrodes. The spacer is bonded to the substrate via an insulating layer, for example. The first and the second opposed electrodes are electrically connected to the third and the fourth leads respectively, via through holes formed in the insulating layer. On the other hand, the first and the second electrodes are formed on the substrate, and are electrically connected to the first and the second leads. This construction allows individual measurements, i.e. the measurement of the physical quantity correlating to e.g. dielectric coefficient using the first and the second opposed electrodes and the measurement of the physical quantity correlating to concentration of a specific component using the first and the second electrodes.

The first and the second opposed electrodes can also be used in the measurement of a responding current value correlating to concentration of a specific component in the specimen liquid. In this case, the first and the second opposed electrodes may be used in a measurement of a physical quantity correlating to dielectric coefficient, resistance value or electric conductivity of the specimen liquid.

A second aspect of the present invention provides an analyzing device which uses an analyzing implement, for measurement of concentration of a specific component in the specimen liquid. The analyzing implement includes: a capillary for movement of the specimen liquid; a first and a second opposed electrodes opposed to each other in an inner surface of the capillary for measurement of a first physical quantity correlating to dielectric constant, resistance value or electric conductivity of the specimen liquid; and a first and a second electrodes for measurement of a second physical quantity correlating to concentration of a specific component in the specimen liquid. The analyzing device includes: DC voltage applying means for applying a DC voltage between the first and the second electrodes; AC voltage applying means for applying an AC voltage between the first and the second opposed electrodes; first measuring means for measuring the first physical quantity; second measuring means for measuring the second physical quantity; and calculating means for calculating a concentration level of a specific component in the specimen liquid based on the first physical quantity measured by the first measuring means.

The analyzing device according to the present aspect preferably further includes switching means for selecting between a first state in which the AC voltage applying means and the first measuring means are electrically connected to the first and the second opposed electrodes and a second state in which the DC voltage applying means and the second measuring means are electrically connected to the first and the second electrodes.

A third aspect of the present invention provides an analyzing device which uses an analyzing implement, for measurement of concentration of a specific component in the specimen liquid. The analyzing implement includes: a capillary for movement of the specimen liquid; a first and a second opposed electrodes opposed to each other in an inner surface of the capillary. The first and the second opposed electrodes serve in measurement of a first physical quantity correlating to dielectric constant, resistance value or electric conductivity of the specimen liquid, as well as in measurement in a second physical quantity correlating to concentration of a specific component in the specimen liquid. The analyzing device includes: DC voltage applying means for applying a DC voltage between the first and the second electrodes; AC voltage applying means for applying an AC voltage between the first and the second opposed electrodes; first measuring means for measuring the first physical quantity; second measuring means for measuring the second physical quantity; and calculating means for calculating a concentration level of a specific component in the specimen liquid based on the first physical quantity measured by the first measuring means.

The analyzing device according to the present aspect preferably further includes switching means for selecting between a first state in which the AC voltage applying means and the first measuring means are electrically connected to the first and the second opposed electrodes and a second state in which the DC voltage applying means and the second measuring means are electrically connected to the first and the second electrodes.

According to the second and the third aspects of the present invention, preferably, the calculating means calculates the concentration level of the specific component in the specimen liquid while taking into account the second physical quantity measured by the second measuring means.

BEST MODE FOR CARRYING OUT THE INVENTION

Now, a first mode of embodiment of the present invention will be described with reference to FIG. 1 through FIG. 6.

Figure 1:
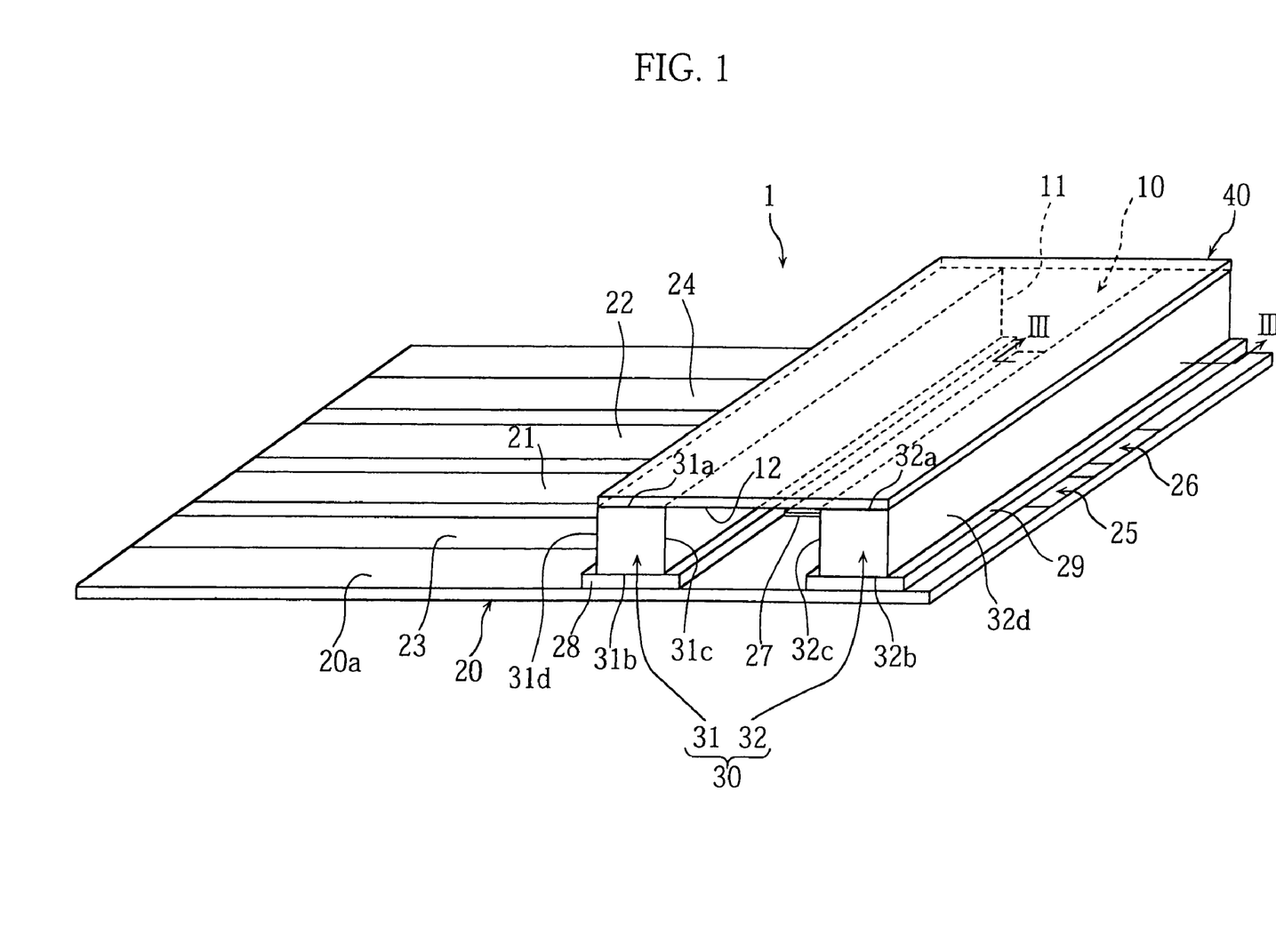
FIG. 1 is an overall perspective view showing a biosensor according to a first embodiment of the present invention.
Figure 2:
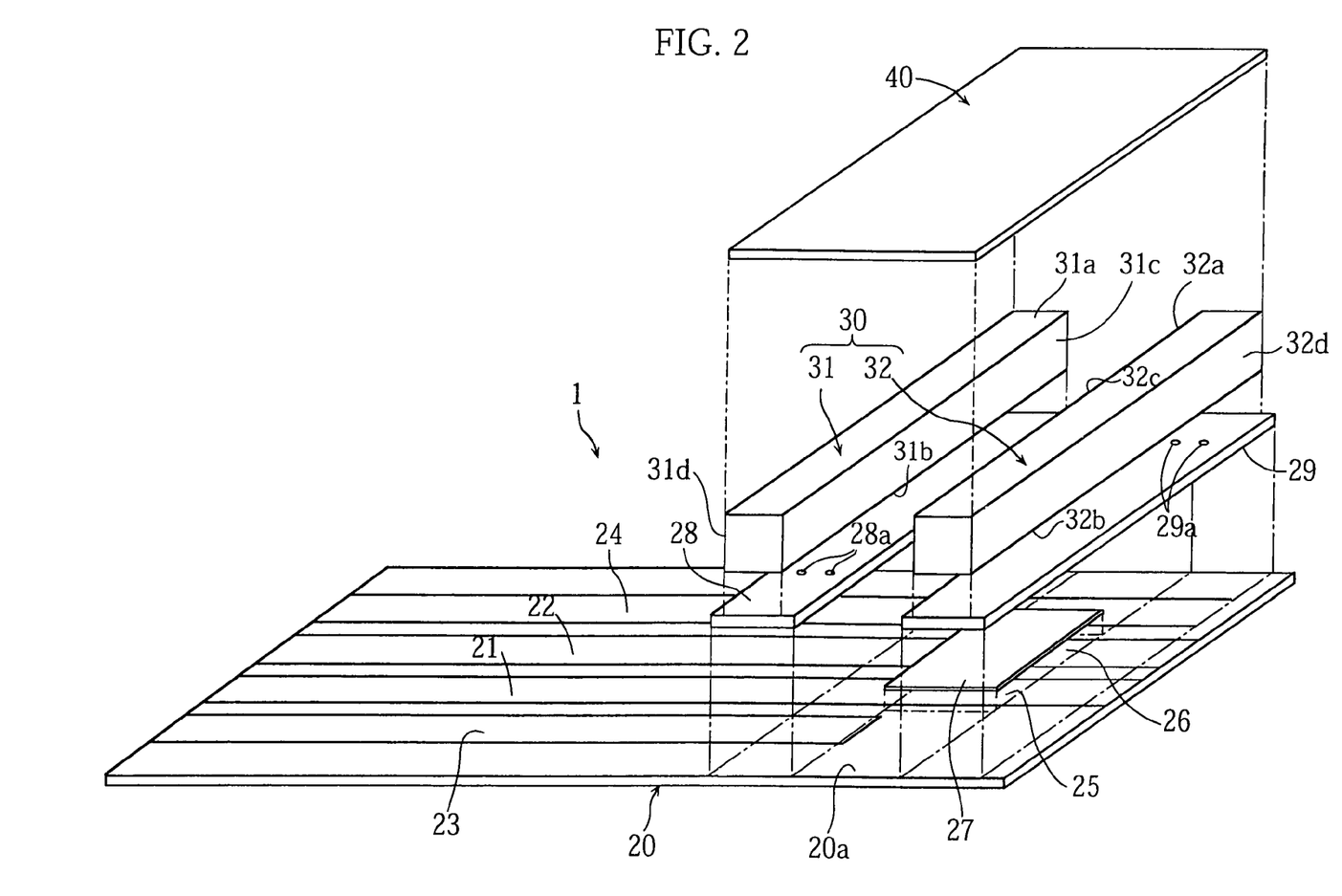
FIG. 2 is an exploded perspective view of the biosensor in FIG. 1.

A biosensor 1 shown in FIG. 1 and FIG. 2 is for a measurement of a blood glucose level, and is used as attached to an analyzing device 5 to be detailed later with reference to FIG. 4. The biosensor 1 includes a substrate 20, a cover 40 laminated thereon, and a spacer 30 in between. These members 20, 30 and 40 form a capillary 10. The capillary 10 introduces the blood from an open end 11, allows the blood to move and stay within, under the principle of capillarity. The capillary 10 has another open end 12 in order to release gas from within the capillary 10 when introducing the blood into the capillary 10.

The spacer 30 includes a pair of blocks 31, 32 opposed to each other. These blocks 31, 32 serve as electrodes for applying an AC voltage to the blood when measuring a resistance value of the blood. The blocks 31, 32 have upper surfaces 31a, 32a, lower surfaces 31b, 32b, and two side surfaces 31c, 32c and 31d, 32d respectively. Each block has a rectangular section, and the whole block is electrically conductive. Therefore, the electrodes for applying AC voltage to the blood are opposed to each other. The blocks 31, 32 can be formed of an electrically conductive polymer, a resin containing an electrically conductive filler, or a metal.

The upper surfaces 31a, 32a and the lower surfaces 31b, 32b of the blocks 31, 32 are adhesive. The adhesiveness of the upper surfaces 31a, 32a and the lower surfaces 31b, 32b is used to bond the cover 40 onto the substrate 20.

The substrate 20 is rectangular. The substrate 20 has an upper surface 20a formed with a first through fourth leads 21-24, each extending longitudinally of the substrate 20. Further, the upper surface 20a of the substrate 20 is provided with a first and a second electrodes 25, 26 and a reactor 27. The reactor 27 is solid for example, and bridges the first and the second electrodes 25, 26. The reactor 27 includes, for example, an oxidation-reduction enzyme and an electron transfer material. The oxidation-reduction enzyme is provided by glucose oxidase or glucose dehydrogenase for example, whereas the electron transfer material is provided by potassium ferricyanide for example.

The first and the second leads 21, 22 are for application of a voltage between the first and the second electrodes 25, 26. The first lead 21 is formed integrally with the first electrode 25, and the second lead 22 is formed integrally with the second electrode 26.

The third and the fourth leads 23, 24 are for application of a voltage between the two blocks 31, 32. The third lead 23 is electrically connected to the block 31, and the fourth lead 24 is electrically connected to the block 32.

The blocks 31, 32 are bonded to the substrate 20, via insulating layers 28, 29 respectively. The insulating layer 28 covers the first through the fourth leads 21-24 whereas the insulating layer 29 covers the first, the third and the fourth leads 21, 22, 23.

The insulating layers 28, 29 are formed with through holes 28a, 29a. The blocks 31, 32 are connected to the third lead 23 or the fourth lead 24 via the through holes 28a, 29a. It should be noted however, that electrical connection between the blocks 31, 32 and the relevant third lead 23 or fourth lead 24 may be established any other way, without being limited by the use of the through holes 28a, 29a.

According to the biosensor 1, capillarity allows the blood to come in from the open end 11 of the capillary 10 and move toward the open end 12 of the capillary 10. During this movement, the blood solves the reactor 27. The introduction of the blood continues until the blood reaches the open end 12, i.e. until the blood has filled the capillary 10. As a result, a liquid-phase reaction system is established inside the capillary 10.

Figures 3, 4:
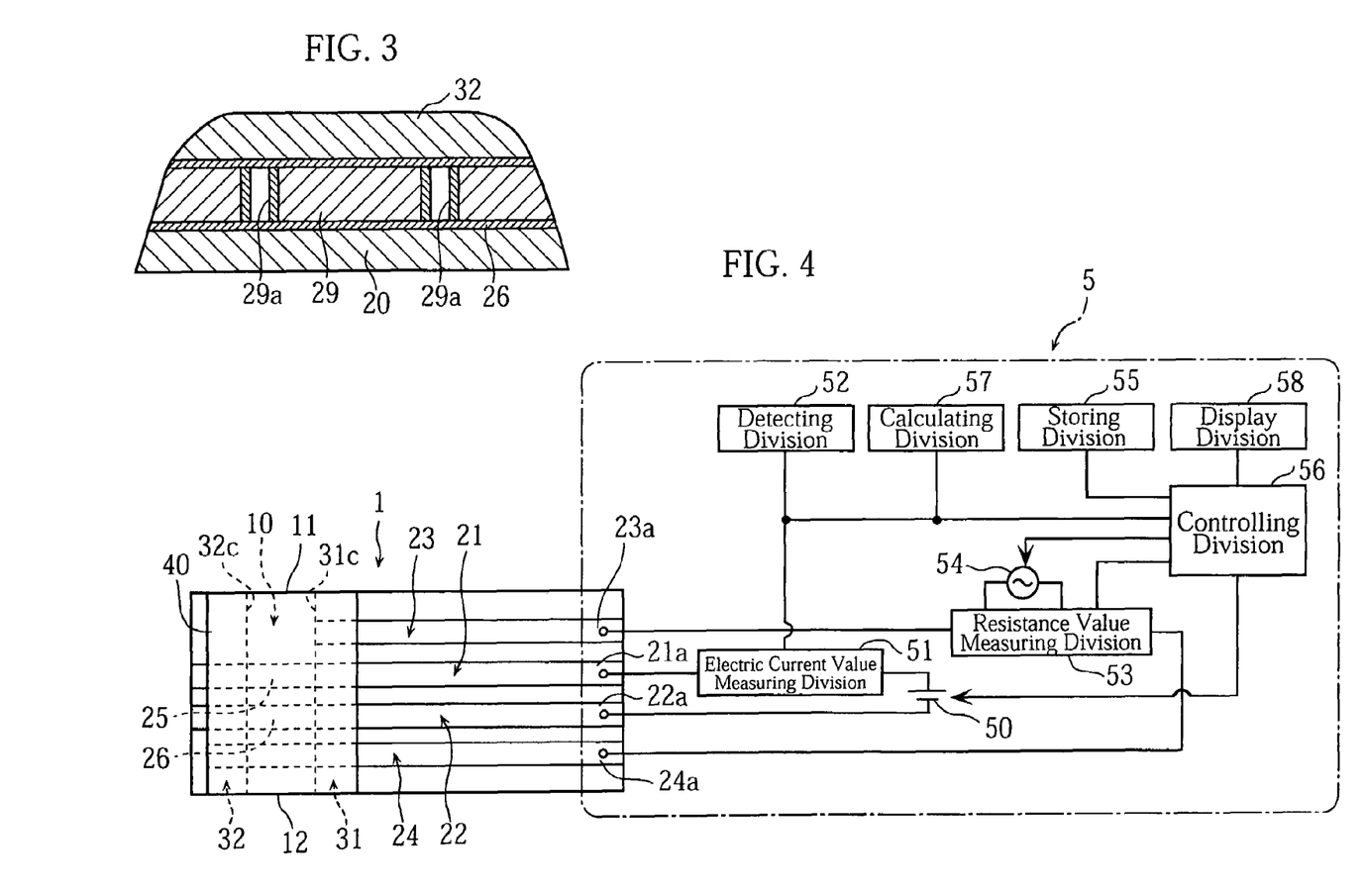
FIG. 3 is a sectional view taken in lines III-III in FIG. 1.
FIG. 4 is a plan view of the biosensor as attached to an analyzing device according to the first embodiment, and a block diagram of the analyzing device.

As shown in FIG. 4, an analyzing device 5 includes a DC power source 50, an electric current value measuring division 51, a detecting division 52, a resistance value measuring division 53, an AC power source 54, a storing division 55, a controlling division 56, a calculating division 57 and a display division 58.

The DC power source 50 applies a DC voltage between the first and the second electrodes 25, 26 via ends 21a, 22a of the first and the second leads 21, 22. The DC power source 50 is electrically connected with the ends 21a, 22a when the biosensor 1 is attached to the analyzing device 5. The DC power source 50 can be provided by a dry battery or a rechargeable battery.

The electric current value measuring division 51 measures a value of responding current when the DC voltage is applied between the first and the second electrodes 25, 26.

The detecting division 52 detects, after the biosensor 1 is attached to the analyzing device 5, if the blood has been supplied inside the capillary 10. The detecting division 52 checks whether or not an electric current value detected by the electric current value measuring division 51 exceeds a predetermined threshold value, thereby determining whether or not the blood has been introduced.

Figure 5:
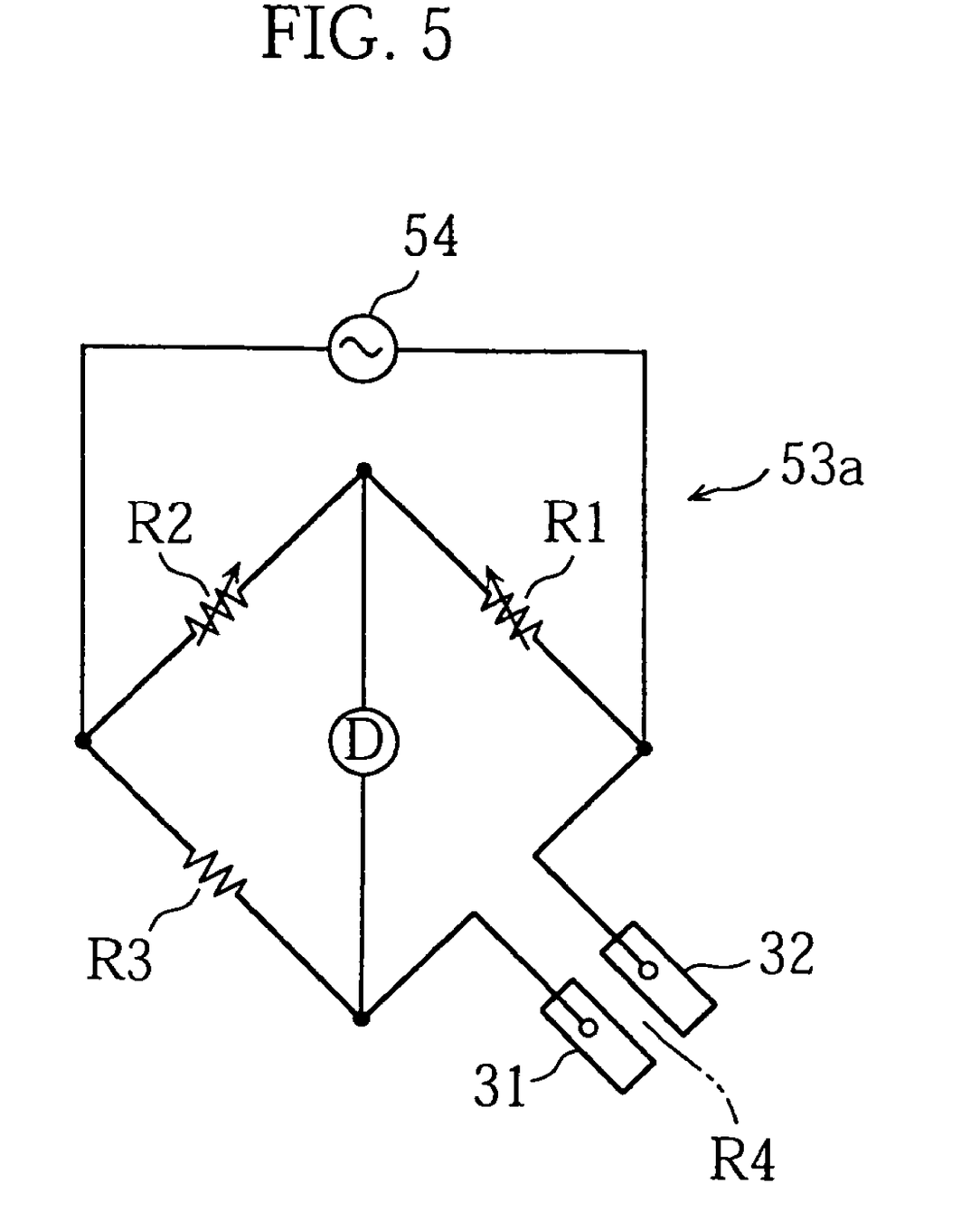
FIG. 5 is a circuit diagram for describing a resistance value measuring circuit.

The resistance value measuring division 53 measures a resistance value of the blood (the liquid-phase reaction system) held in the capillary 10. Resistance values of blood correlate with the amount of ionized component, i.e. percentage of blood cells (hematocrit value) in the blood. Therefore, by measuring a resistance value of the blood, a hematocrit value can be calculated and a level of influence from the hematocrit value can be estimated. The resistance value measuring division 53 includes a measuring circuit 53a shown in FIG. 5. The measuring circuit 53a constitutes a Wheatstone bridge circuit together with the blocks 31, 32 and other members. The measuring circuit 53a includes three resisters R1-R3 and a balance detector D. The resistors R1, R2 are variable resistors. Blood held in the capillary 10 is represented by a resistor R4 in the figure. The measuring circuit 53a controls resistance values of the variable resistors R1, R2 so that there is no current flowing through the balance detector D, and a measurement is made for a blood resistance value on the basis of the controlled resistance values of the R1, R2 and a known value of the resistor R3. Specifically, the blood resistance value r4 is given by the following formula, where resistance values of the resistors R1 through R4 are represented by r1 through r4 respectively.

$$r4 = r1 \times r3 / r2$$

Alternatively, circuits different from the measuring circuit 53a in FIG. 5 may be constructed for measurement of blood dielectric constant or electric conductivity, for calculation of hematocrit values or estimation of the level of influence from the hematocrit values.

The AC power source 54 applies an AC voltage between the blocks 31, 32 and to the measuring circuit 53a. The application of the AC voltage between the two blocks 31, 32 is made via the ends 23a, 24a of the third and the fourth leads 23, 24.

The storing division 55 stores a control program for controlling the DC power source 50, the AC power source 54 and so on, calibration curve data used in calculating blood glucose levels, a calculation program for calculating the glucose levels, a resistance calculation program for calculating the resistance value r4, correction data for the calculated value to be corrected on the basis of the given resistance value r4, and a correction program for correcting the calculated value. The calibration curve data or the correction data is stored in the form of lookup table which indicates a relationship between, for example, the value of responding current and the glucose level or between the resistance value r4 and the corrected value. The storing division 55 is provided by a ROM or a RAM.

The controlling division 56 is provided by a CPU for example, and controls voltage application from the DC power source 50 and the AC power source 54, as well as operation of the divisions 52, 53 and 58.

The calculating division 57 calculates a blood glucose level based on the responding current value measured by the electric current value measuring division 51, and corrects the calculated value, on the basis of the resistance value measured by the resistance value measuring division 53.

The display division 58 displays the glucose level and other information, and is provided by a liquid crystal display for example.

Figure 6:
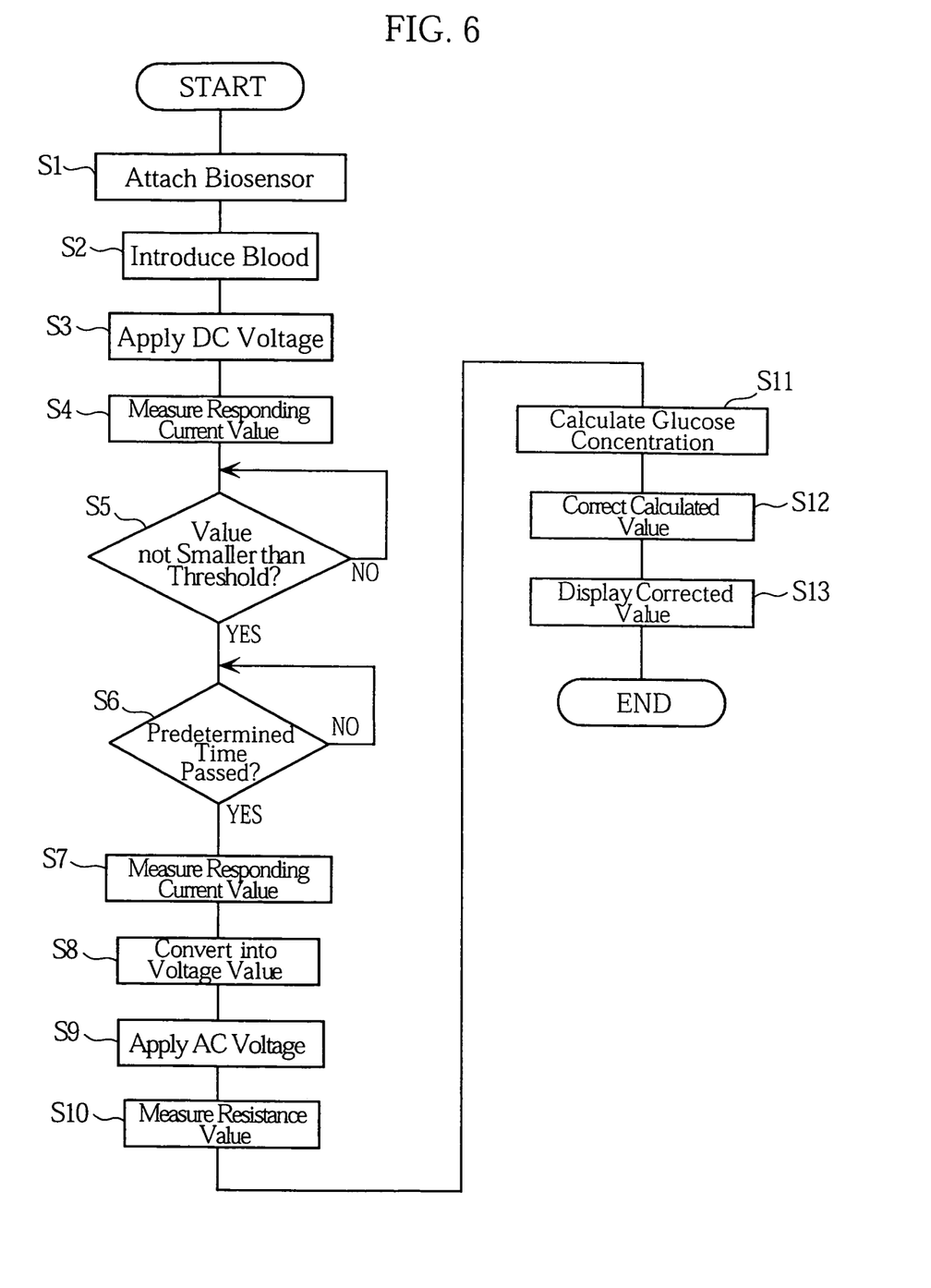
FIG. 6 is a flowchart for describing a concentration level measuring operation.

Hereinafter, description will cover how a blood sugar level is measured by the biosensor 1 and the analyzing device 5, with reference to FIG. 1 through FIG. 5 as well as a flowchart in FIG. 6.

When measuring the blood sugar level, first, the biosensor 1 is attached to an analyzing device 5 (S1), and blood is introduced into the capillary 10 (S2).

Meanwhile, the controlling division 56 applies a DC voltage between the first and the second electrodes 25, 26 (S3). At this time, the electric current value measuring division 51 measures a value of responding current (S4). The measurement of the responding current value is made per 0.05-0.2 seconds for example. The detecting division 52 monitors the responding current values measured at the electric current value measuring division 51, and checks if the responding current value is not smaller than a threshold value (S5).

When the detecting division 52 sees that the responding current value is not smaller than the threshold value (S5: YES), the detecting division 52 determines that the blood has been introduced into the capillary 10. On the other hand, if the detecting division 52 sees that the responding current value is not greater than the threshold value (S5: NO), the detecting division 52 continues the check in Step S5. However, if the detecting division 52 continues to see the responding current value being smaller than the threshold value after a lapse of a predetermined duration of time (S5: NO), then the program may execute an error processing routine.

When blood is introduced into the capillary 10, a liquid-phase reaction system is established as described earlier. In this liquid-phase reaction system, the glucose is oxidized while the electron transfer material is reduced. The electron transfer material is then oxidized when a DC voltage is applied, and a quantity of electrons released per a unit of time can be measured as a responding current value.

When the detecting division 52 has determined that the responding current value is not smaller than the threshold value (S5: YES), then the controlling division 56 checks if a predetermined amount of time (e.g. 5-30 seconds) has passed since the time when the responding current exceeded the threshold value (S6). This check in Step S6 is repeated until the controlling division 56 sees that the predetermined amount of time has passed (S6: YES).

When the controlling division 56 sees that the predetermined amount of time has passed (S6: YES), the electric current value measuring division 51 measures the responding current value (S7), and the measured responding current value is converted into a voltage value (S8).

Meanwhile, in parallel to the application of the DC voltage, the controlling division 56 applies an AC voltage between the blocks 31 and 32 (S9) while allowing the resistance value measuring division 53 to measure a blood resistance value (S10). The measurement of the resistance value is made after the detecting division 52 has detected introduction of the blood into the capillary 10.

The calculating division 57 calculates a glucose concentration level (S11) with reference to the calibration curve data stored in the storing division 55 and based on the voltage value given by the conversion in Step S8. Then, the calculating division 57 corrects the calculated value, based on the resistance value measured by the resistance value measuring division 53. The correction of the calculated value is made by referring to the correction data stored in the storing division 55. The corrected value is displayed in the display division 58.

The display division may display, in addition to the corrected value, a hematocrit value which can be calculated from the pre-correction calculation or from the resistance value. Alternatively, both of the pre-correction value and the hematocrit value may be displayed.

According to the present embodiment, a DC voltage can be applied to the biosensor 1 or between the first and the second electrodes 25, 26, whereas an AC voltage can be applied between the blocks 31, 32. Therefore, it is possible to measure a responding current value which is necessary for calculating the glucose level and a resistance value which is necessary for correcting the calculated value, with a single biosensor 1. This provides a cost advantage in measurement, to the extent that there is no need for separate preparation of an analyzing implement for measuring glucose level and an analyzing implement for measuring hematocrit value (resistance value). Further, this provides an improved operability to the extent that there is no need for replacing an analyzing implement necessary for glucose level measurement with an analyzing implement necessary for hematocrit value measurement in order to allow measurement of a hematocrit value.

The biosensor 1 uses the blocks 31, 32 as electrodes for measuring a resistance value. According to the described construction, the object of measurement, i.e. the liquid-phase reaction system (the capillary 10) has an area of the section which is generally equal to an area of the opposed surface in the blocks (electrodes) 31, 32, making possible to make uniform distribution of the electric lines of force. This makes possible to measure a value of resistance in the liquid-phase reaction system (blood) at a high accuracy, leading to accurate measurement of a blood sugar level regardless of the hematocrit value.

According to the biosensor 1, application of a DC voltage between the first and the second electrodes 25, 26 and application of an AC voltage between the blocks 31, 32 can be made separately and simultaneously. Therefore, according to the biosensor 1, the amount of time necessary for measurement is not long even if a measurement is made for a resistance value in addition to a responding current.

Next, a second embodiment of the present invention will be described with reference to FIG. 7. It should be noted that in FIG. 7, elements identical with those used in the biosensor according to the first embodiment are given the same alpha-numeric codes, and their description will not be repeated hereinafter.

Figure 7:
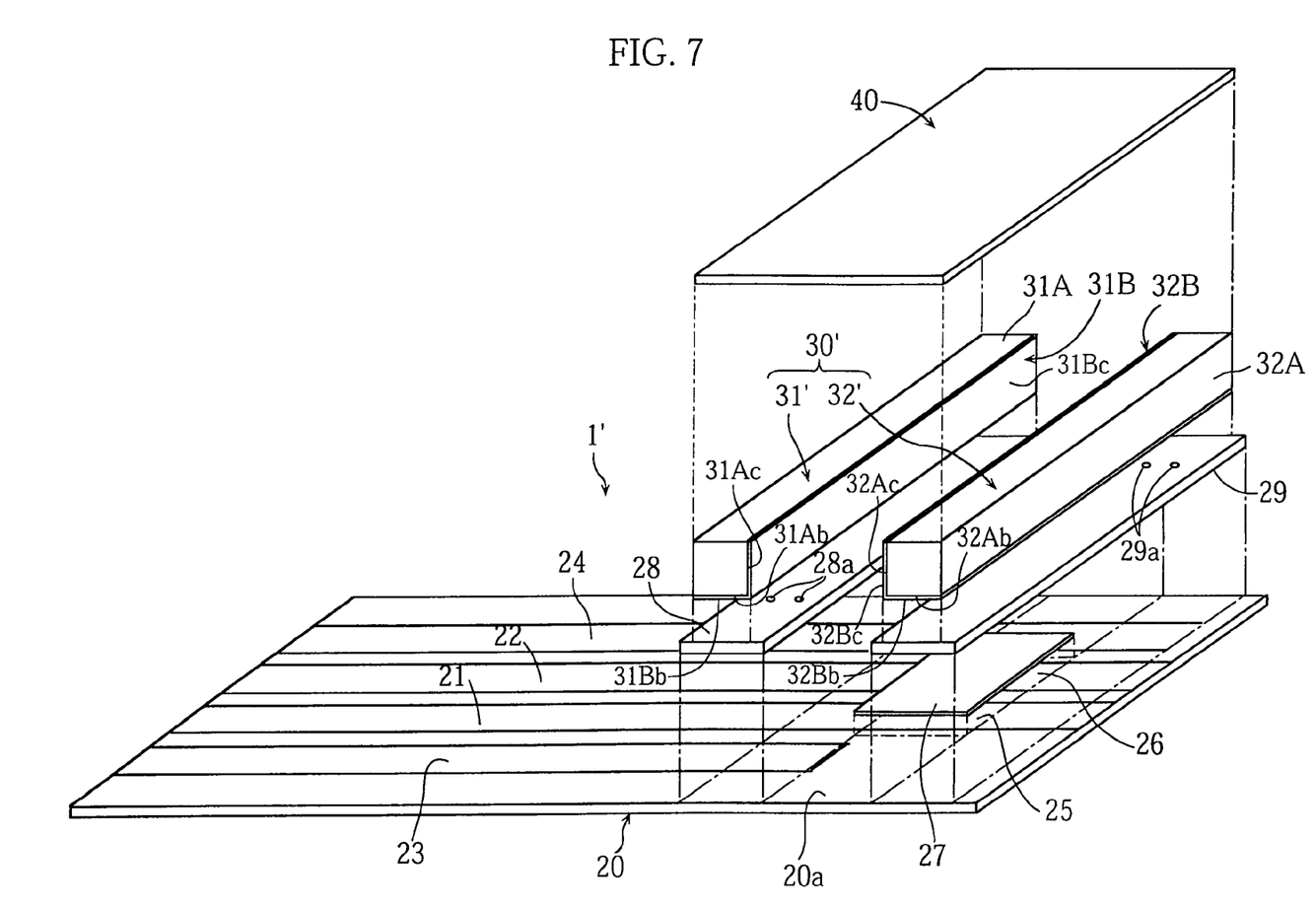
FIG. 7 is an exploded perspective view of a biosensor according to a second embodiment of the present invention.

A biosensor 1' shown in FIG. 7 includes a spacer 30' (two blocks 31', 32') which has a different construction from the one used in the biosensor 1 according to the first embodiment (See FIG. 1 and FIG. 2).

The blocks 31', 32' include insulating members 31A, 32A each having a rectangular cross section. The insulating members 31A, 32A have surfaces formed with conductive layers 31B, 32B respectively.

The conductive layers 31B, 32B respectively have: first regions 31Bc, 32Bc which cover side surfaces 31Ac, 32Ac of the insulating members 31A, 32A; and second regions 31Bb, 32Bb which continue from the first regions 31Bc, 32Bc and cover lower surfaces 31Ab, 32Ab of the insulating members 31A, 32A. The first regions 31Bc, 32Bc are opposed to each other, and serve as a pair of opposed electrodes for measurement of blood resistance values. The second regions 31Bb, 32Bb are connected to the third and the fourth lead 23, 24 respectively, and are used together with the third and the fourth leads 23, 24, to apply a voltage between the opposed electrodes (the first regions 31Bc, 32Bc).

The biosensor 1' can be attached to the analyzing device 5 shown in FIG. 4, and by introducing blood into the capillary, measurements can be made for a responding current value which is necessary for glucose level calculation and a resistance value which is necessary for correction of the calculated value. Further, since electrodes for measuring the resistance value are opposed to each other, and an area of the opposed surface is generally equal to an area of the cross section of the liquid-phase reaction system, accurate measurement of the resistance value is possible.

Next, a third embodiment of the present invention will be described with reference to FIG. 8 and FIG. 9. It should be noted that in FIG. 8 and FIG. 9, elements identical with those used in the biosensor or the analyzing device according to the first embodiment are given the same alpha-numeric codes, and their description will not be repeated hereinafter.

Figure 8:
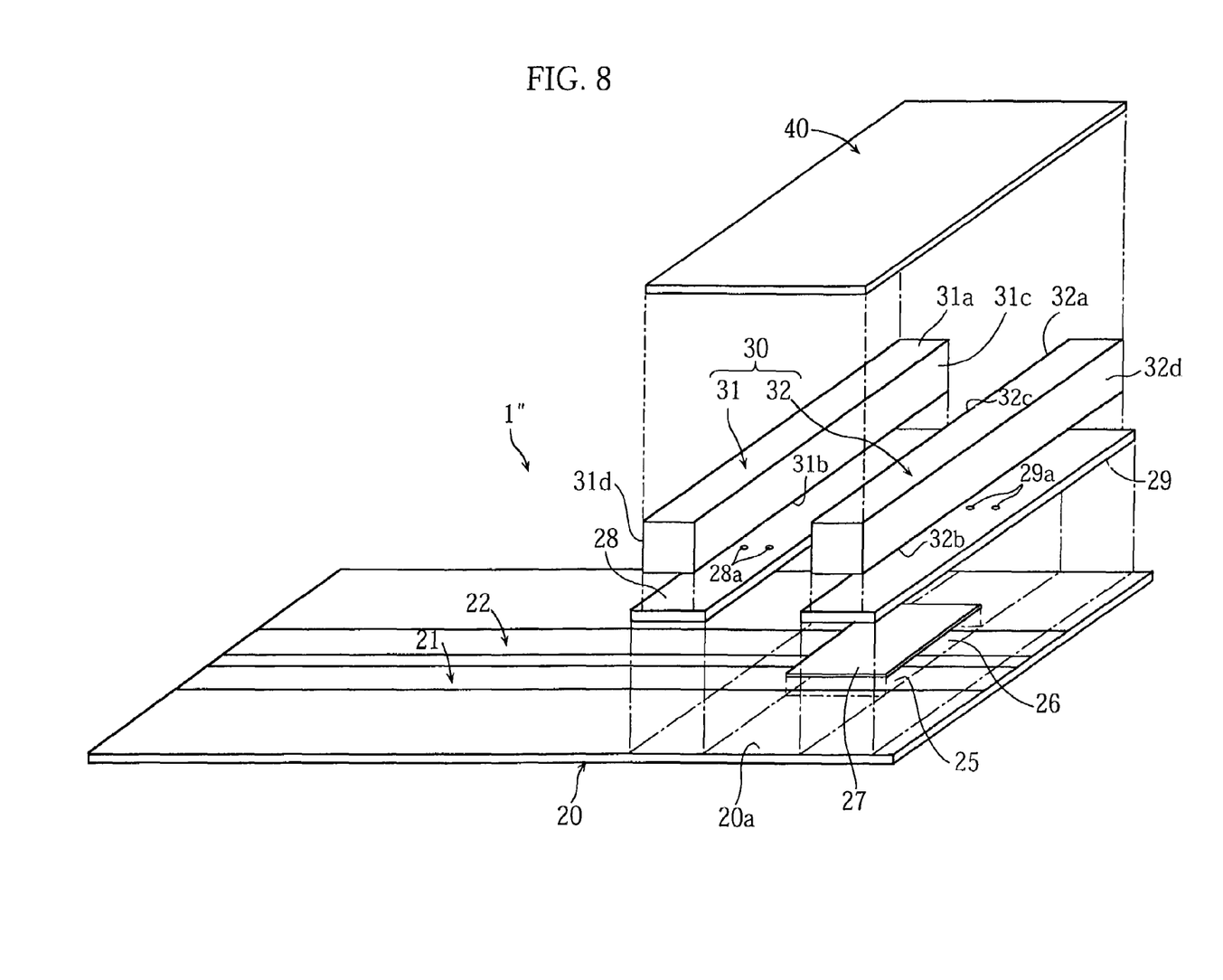
FIG. 8 is an exploded perspective view of a biosensor according to a third embodiment of the present invention.

In a biosensor 1" shown in FIG. 8, the first and the second leads 21, 22 used for the application of DC voltage to the first and the second electrode 25, 26 are also used for the application of AC voltage to the blocks 31, 32.

Figure 9:
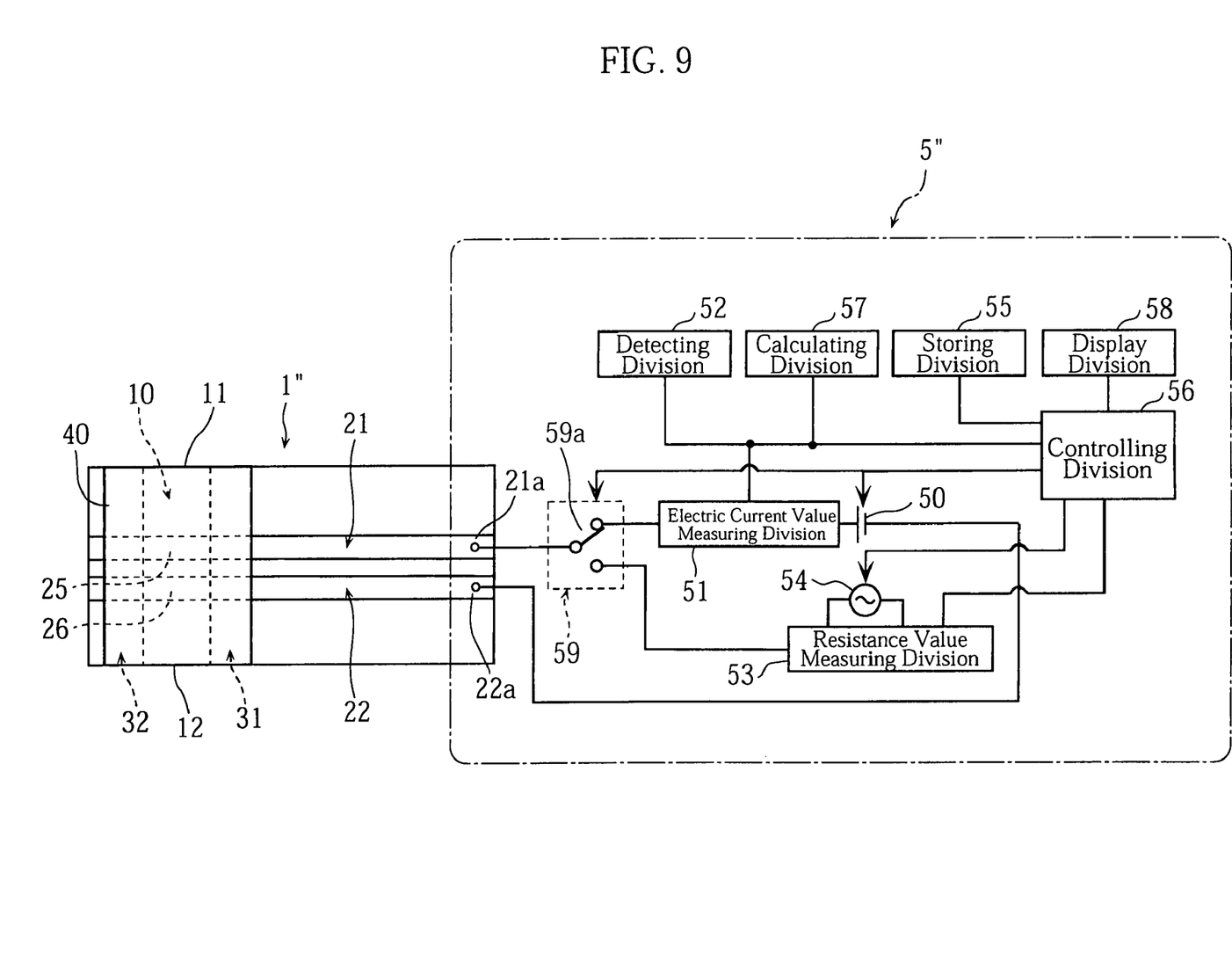
FIG. 9 is a plan view of the biosensor as attached to an analyzing device according to the third embodiment, and a block diagram of the analyzing device.

Correspondingly, an analyzing device 5' shown in FIG. 9 includes a switching division 59 for selection whether the first and the second leads 21, 22 are electrically connected to the DC power source 50 or to the AC power source 54. The switching division 59 has a switch 59a, so that the controlling division 56 controls the switch 59a thereby selecting different states of voltage application to the liquid-phase system.

When measuring a responding current value, the switch 59a establishes connection with the electric current value measuring division 51, based on the control by the controlling division 56. This allows the DC power source 50 to apply a DC voltage to the liquid-phase system in the capillary 10, and a responding current value is measured by the electric current value measuring division 51. On the other hand, when measuring a resistance value, the switch 59a establishes connection with the resistance value measuring division 53, based on the control by the controlling division 56. This allows the AC power source 54 to apply an AC voltage to the liquid-phase system in the capillary 10, and a resistance value is measured by the resistance value measuring division 51.

According to the present invention, the blocks (opposed electrodes) may be used for both measurements; the measurement of a resistance value of the specimen liquid and the measurement of a responding current value. In this case, portions representing the first and the second electrodes 25, 26 in the biosensor are covered by an electrically insulating layer.

The present invention can also provide an analyzing implement only for a measurement of a resistance value of a specimen liquid (e.g. hematocrit value of blood). Such an implement is simply the biosensor in FIG. 8 less the reaction division.

The present invention is not limited to the embodiments so far described. For example, the spacer may include only one member provided with a slit for formation of a capillary. The application of an AC voltage between the blocks may be made from end faces of the blocks.

The invention claimed is:

1. An analyzing implement comprising a substrate, a cover covering the substrate, a spacer disposed between the substrate and the cover, and a capillary for movement of a specimen liquid, wherein the capillary is formed by the substrate, the cover and the spacer, wherein the capillary has an inner surface provided with first and second opposed electrodes opposed to each other, wherein the surfaces of the spacer forming the capillary are electrically conductive and provide the first and second opposed electrodes, and wherein the spacer includes two blocks opposed to each other, the two blocks being formed entirely of an electrically conductive material.

2. The analyzing implement according to claim 1, wherein the two blocks are formed of an electrically insulating resin containing an electrically conductive polymer or an electrically conductive filler.

3. The analyzing implement according to claim 1, wherein each of the two blocks has a rectangular cross section defined by an upper surface, a lower surface and two side surfaces, the upper surfaces and the lower surfaces being adhesive, the cover being bonded to the substrate via the two blocks.

4. The analyzing implement according to claim 1, wherein the first and second opposed electrodes are for measurement of a dielectric constant, a resistance value or a physical quantity correlating to electrical conductivity of the specimen liquid.

5. The analyzing implement according to claim 4, further comprising first and second flat electrodes for measurement of a physical quantity correlating to concentration of a specific component of the specimen liquid.

6. The analyzing implement according to claim 5, further comprising a first lead electrically connected to the first opposed electrode and to the first flat electrode, and a second lead connected to the second opposed electrode and to the second flat electrode.

7. The analyzing implement according to claim 6, further comprising first through fourth leads formed on the substrate, the spacer being bonded to the substrate via an insulating layer, the first and second flat electrodes being formed on the substrate and electrically connected to the first and second leads respectively, the first and second opposed electrodes being electrically connected to the third and fourth leads respectively, via through holes formed in the insulating layer.

8. The analyzing implement according to claim 1, wherein the first and the second opposed electrodes serve in measurement of a responding current value correlating to concentration of a specific component in the specimen liquid.

9. An analyzing implement comprising a substrate, a cover covering the substrate, a spacer disposed between the substrate and the cover, a capillary for movement of a specimen liquid, and first and second leads formed on the substrate, the capillary being formed by the substrate, the cover and the spacer, the capillary having an inner surface provided with first and second opposed electrodes opposed to each other surfaces of the spacer forming the capillary being electrically conductive and providing the first and the second opposed electrodes, the spacer being bonded to the substrate via an insulating layer., the first and the second opposed electrodes being electrically connected to the first and the second leads respectively, via through holes formed in the insulating layer.

10. An analyzing implement comprising a capillary for movement of a specimen liquid, wherein the capillary has an inner surface provided with first and second opposed electrodes opposed to each other for measurement of a dielectric constant, a resistance value or a physical quantity correlating to electrical conductivity of the specimen liquid, wherein the analyzing implement further comprises first and second flat electrodes for measurement of a physical quantity correlating to concentration of a specific component of the specimen liquid, a first lead electrically connected to the first opposed electrode and to the first flat electrode, and a second lead connected to the second opposed electrode and to the second flat electrode.

* * * * *